(12) United States Patent
Feng et al.

(10) Patent No.: US 10,627,406 B2
(45) Date of Patent: Apr. 21, 2020

(54) METHOD AND KIT FOR DETECTING GLUTATHIONE

(71) Applicant: Kaohsiung Medical University, Kaohsiung (TW)

(72) Inventors: Chia-Hsien Feng, Kaohsiung (TW); Chen-Wen Chen, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 222 days.

(21) Appl. No.: 15/878,944

(22) Filed: Jan. 24, 2018

(65) Prior Publication Data
US 2018/0238900 A1 Aug. 23, 2018

Related U.S. Application Data

(60) Provisional application No. 62/460,452, filed on Feb. 17, 2017.

(30) Foreign Application Priority Data

Jul. 3, 2017 (TW) .............................. 106122222 A

(51) Int. Cl.
*G01N 33/68* (2006.01)
*G01N 33/48* (2006.01)

(52) U.S. Cl.
CPC ............. *G01N 33/68* (2013.01); *G01N 33/48* (2013.01); *G01N 2410/00* (2013.01); *Y10T 436/25* (2015.01)

(58) Field of Classification Search
CPC .... G01N 2410/00; G01N 33/48; G01N 33/68; Y10T 436/145555; Y10T 436/19;
(Continued)

(56) References Cited

U.S. PATENT DOCUMENTS

2012/0196375 A1* 8/2012 Granja ............... G01N 21/6428
436/94

FOREIGN PATENT DOCUMENTS

| CN | 101329345 A | 12/2008 |
|---|---|---|
| CN | 103512855 A | 1/2014 |
| WO | WO2009/018112 A2 | 2/2009 |

OTHER PUBLICATIONS

Chen et al. Talanta, vol. 199, pp. 464-471, Feb. 27, 2019.*
Feng et al. Analytica Chimica Acta, vol. 690, pp. 209-214, Feb. 12, 2011.*

* cited by examiner

*Primary Examiner* — Maureen Wallenhorst
(74) *Attorney, Agent, or Firm* — WPAT, PC

(57) ABSTRACT

A method for detecting glutathione includes mixing a sample including glutathione, 9-bromomethyl acridine (Br-MA) and a derivatization solvent to form a reaction solution. A derivative reaction occurs between Br-MA and glutathione to obtain a derivatization solution including a glutathione derivative with a thiol group being substituted with a tag. Excess Br-MA is removed by adding an interference removing solvent into the derivatization solution, followed by vortexing and centrifugation to obtain an aqueous layer solution. The aqueous layer solution is used as an analytic solution, and the glutathione derivative in the analytic solution is detected to obtain a glutathione value. The present invention also provides a kit for detecting glutathione which is adapted to carry out the method for detecting glutathione.

21 Claims, 10 Drawing Sheets

(58) Field of Classification Search
CPC ................ Y10T 436/24; Y10T 436/25; Y10T 436/25375; Y10T 436/255
USPC ..... 436/86, 96, 124, 63, 164, 172, 161, 173, 436/174, 177, 178; 422/430, 82.05, 422/82.08, 70, 527, 533
See application file for complete search history.

METHOD AND KIT FOR DETECTING GLUTATHIONE

CROSS REFERENCE TO RELATED APPLICATIONS

The application claims the benefit both of U.S. provisional application No. 62/460,452, filed on Feb. 17, 2017, and Taiwan application serial No. 106122222, filed Jul. 3, 2017, the entire contents of which are incorporated herein by reference.

BACKGROUND OF THE INVENTION

1. Field of the Invention

The present invention generally relates to a method and, more particularly, to a method for detecting glutathione. The present invention also relates to a kit for detecting glutathione applying for the method.

2. Description of the Related Art

Glutathione is an important antioxidant in animals, plants, fungi, and some bacteria and archaea. Glutathione is capable of preventing damage to important cellular components caused by reactive oxygen species (ROS) such as free radicals, peroxides, and heavy metals. Referring to FIGS. 1a & 1b, glutathione exists in both reduced (GSH) and oxidized (GSSG) states. Once oxidative stress increases in an organism, reduced glutathione (GSH) is oxidized by glutathione peroxidase to form oxidized glutathione (GSSG). Therefore, the ratio of GSH to GSSG (GSH/GSSG) within the organism can be used as a measure of oxidative stress, and can be further used to diagnose diseases or conditions such as diabetes, Parkinson's disease and aging.

In a conventional method for detecting glutathione, a glutathione derivative is formed via a derivative reaction between a thiol group (—SH) of glutathione and a derivatization reagent, improving the detecting sensitivity of the conventional method for detecting glutathione. As an example, both N-ethylmaleimide (NEM) and 5,5-dithio-bis-(2-nitrobenzoic acid) (DTNB) can be used as the derivatization reagent. However, the glutathione derivative formed by the former derivatization reagent has a poor stability. The later derivatization reagent has poor derivatization efficiency. Therefore, the subsequent detecting efficacy is decreased. In light of this, the conventional method for detecting glutathione is required to be improved.

SUMMARY OF THE INVENTION

It is therefore an objective of the present invention to provide a method for detecting glutathione, effectively forming a glutathione derivative, which has a great stability and is easily to be detected.

It is another objective of the present invention to provide a kit for detecting glutathione, which is adapted to carry out the method for detecting glutathione.

One embodiment of the present invention discloses a method for detecting glutathione. The method includes mixing a sample including glutathione, 9-bromomethyl acridine (Br-MA) and a derivatization solvent to form a reaction solution. A derivative reaction occurs between Br-MA and glutathione to obtain a derivatization solution including a glutathione derivative with a thiol group being substituted with a tag. Excess Br-MA is removed by adding an interference removing solvent into the derivatization solution, followed by vortexing and centrifugation to obtain an aqueous layer solution. The aqueous layer solution is used as an analytic solution, and the glutathione derivative in the analytic solution is detected to obtain a glutathione value. Preferably, the derivatization solvent is selected from acetone, acetonitrile or dimethyl sulfoxide (DMSO). Accordingly, by the use of Br-MA, the glutathione derivative with great stability is formed together with glutathione and can be detected by any conventional analytical techniques, such as ultra violet spectroscopy, fluorescence spectroscopy, liquid chromatography or mass spectrometry. Therefore, the method for detecting glutathione according to the present invention has great sensitivity, decreasing sample amount.

In an example, the method includes adding a base catalyst into the reaction solution. The derivative reaction then occurs in the reaction solution dissolving the base catalyst to obtain the derivatization solution. Preferably, the base catalyst is selected from sodium hydroxide (NaOH), potassium hydroxide (KOH), sodium bicarbonate ($NaHCO_3$) or potassium bicarbonate ($KHCO_3$). Therefore, by the basic environment providing by the base catalyst, deprotonation of the thiol group is accelerated, helping the progression of the derivative reaction.

In an example, the method includes extracting glutathione derivative in the aqueous layer solution by a cationic surfactant to obtain an extract. The extract is then used as the analytic solution to obtain the glutathione value. Preferably, the interference removing solvent is selected from ethyl acetate (EA), propyl acetate (PA) or tert-butyl acetate (BA), and the cationic surfactant is selected from trioctylmethylammonium chloride (A336), tetraheptylammonium bromide (THepAB) or tetraoctylammonium bromide (TOAB). Therefore, excess Br-MA and hydrolysates of Br-MA (MA-OH) can be removed by the interference removing solvent, and the glutathione derivative can be enriched by the cationic surfactant, the glutathione derivative can be more easily detected to obtain the glutathione value.

In an example, the method includes mixing a blood sample and a protein precipitant to assure proteins in a blood sample form a protein precipitate. The protein precipitate is removed by centrifugation to obtain a supernatant, which is used as the sample. Preferably, the protein precipitant is selected from acetone or acetonitrile. Therefore, proteins in the blood sample can be removed by the protein precipitant, preventing from poor derivatization efficiency due to interference caused by the proteins in the blood sample.

In an example, the method includes breaking a disulfide bond of glutathione in a blood sample by mixing the blood sample and a reductant. A protein precipitate is formed by adding a protein precipitant into the blood sample, in which the disulfide bond of glutathione is broken, and then removed by centrifugation to obtain a supernatant, which is used as the sample. Preferably, the reductant is selected to be dithiothreitol (DTT), and the protein precipitant is selected from acetone or acetonitrile. Therefore, proteins in the blood sample can be removed by the protein precipitant, preventing from poor derivatization efficiency due to interference caused by the proteins in the blood sample. Moreover, the disulfide bond of oxidized glutathione (GSSG) can be broken by the reductant, and the method for detecting glutathione can thus be adapted to detect oxidized glutathione (GSSG).

The other embodiment of the present invention discloses a kit for detecting glutathione, which is used to detect whether glutathione is present in a sample. The kit includes Br-MA, a derivatization solvent and an interference removing solvent. Br-MA is used to form a glutathione derivative, which has a thiol group substituted with a tag, together with glutathione in the sample. The derivatization is a solvent able to dissolve Br-MA and glutathione, and is used to form a reaction solution together with the sample and Br-MA. The interference removing solvent is a solvent immiscible with the reaction solution, and a Log P value of the interference removing solvent ranges from 0.5 to 2.0. Preferably, the derivatization solvent is selected from acetone, acetonitrile or DMSO, and the interference removing solvent is selected from EA, PA or BA. Therefore, the kit can be adapted to carry out the method for detecting glutathione. The glutathione derivative with great stability can be formed by Br-MA together with glutathione, and can be detected by any conventional analytical techniques, such as ultra violet spectroscopy, fluorescence spectroscopy, liquid chromatography or mass spectrometry, according to demands.

In an example, the kit includes a base catalyst. The base catalyst is a base able to dissolve in the derivatization solvent, and is used to provide a basic environment for the derivative reaction. Preferably, the base catalyst is selected from NaOH, KOH, $NaHCO_3$ or $KHCO_3$. Therefore, by the basic environment providing by the base catalyst, deprotonation of the thiol group is accelerated, helping the progression of the derivative reaction.

In an example, the kit includes a cationic surfactant. The cationic surfactant has a carbon number ranging from 25 to 32, and is used to extract the glutathione derivative. Preferably, the cationic surfactant is selected from A336, THepAB or TOAB. Therefore, excess Br-MA and hydrolysates of Br-MA (MA-OH) can be removed by the interference removing solvent, and the glutathione derivative can be enriched by the cationic surfactant, the glutathione derivative can be more easily detected to obtain the glutathione value.

DETAILED DESCRIPTION OF THE INVENTION

Figure 1A:
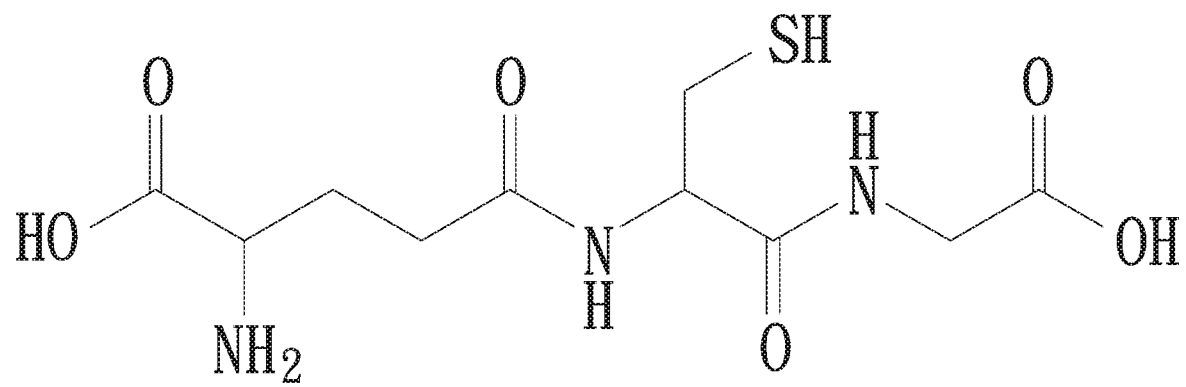
FIG. 1a depicts a chemical structure of reduced glutathione (GSH).
Figure 1B:
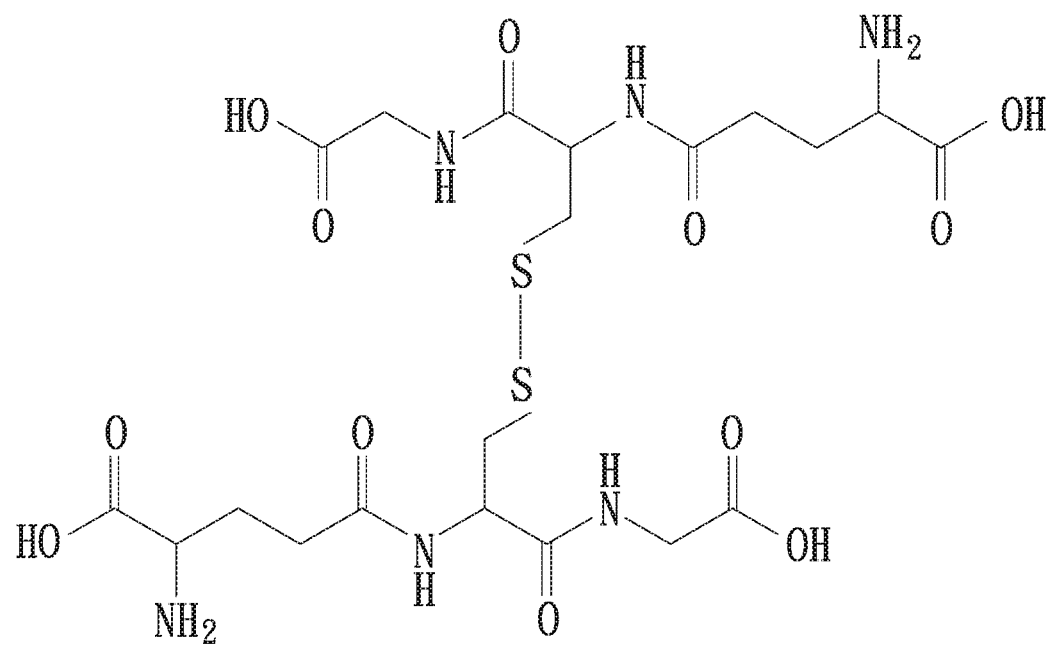
FIG. 1b depicts a chemical structure of oxidized glutathione (GSSG).
Figure 2:
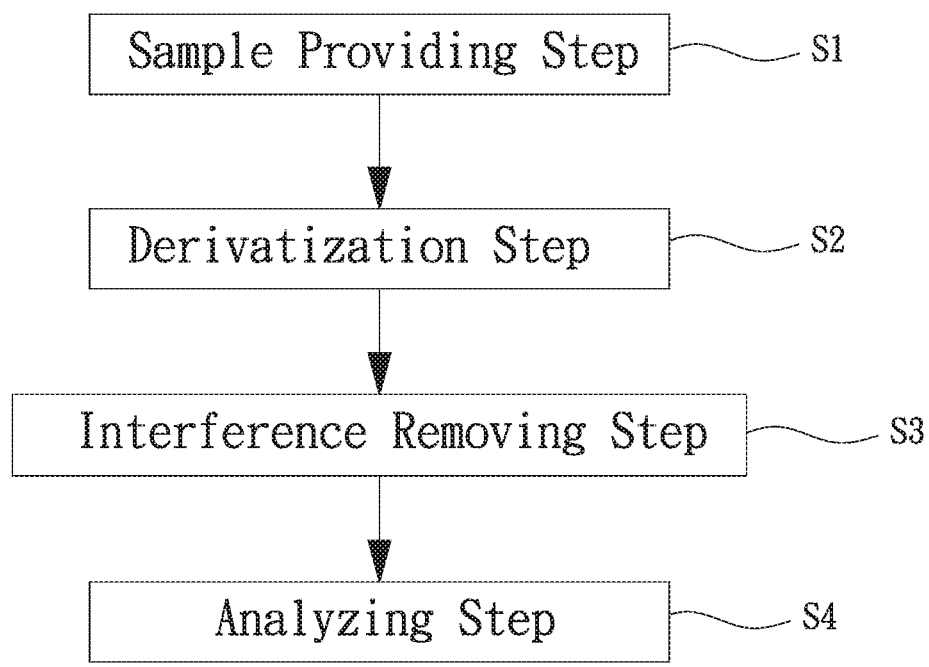
FIG. 2 depicts a flow chart illustrating a method for detecting glutathione according to a first embodiment of the present invention.

Referring to FIG. 2, a method for detecting glutathione according to a first embodiment of the present invention can include a sample providing step S1, a derivatization step S2, an interference removing step S3 and an analyzing step S4. In the sample providing step S1, a sample containing glutathione is provided. In the derivatization step S2, glutathione in the sample forms a glutathione derivative via a derivative reaction together with a derivatization reagent. In the interference removing step S3, excess derivatization reagent is removed. In the analyzing step S4, a glutathione value is obtained by detecting the glutathione derivative.

Specifically, in the sample providing step S1, a drug sample, a cosmetic sample or a food sample can be used as the sample. Alternatively, a blood sample, such as a whole blood sample, a plasma sample or a red blood cell (RBC) sample, derived from mammals can also be used as the sample.

It is worthy to noted that before the derivatization step S2, proteins in the blood sample should be removed to prevent from poor derivatization efficiency due to interference caused by the proteins in the blood sample. As an example, the blood sample can be mixed with a protein precipitant, and the proteins in the blood sample form a protein precipitate, which can be removed by centrifugation at 14,800 rpm for 1 minute to obtain a supernatant. The supernatant can be used as the sample in the following derivatization step S2. In this embodiment, acetone or acetonitrile (ACN) can be used as the protein precipitant.

Moreover, the method for detecting glutathione according to the first embodiment can also be adapted to detect oxidized glutathione (GSSG). In this situation, a reductant is used to break a disulfide bond (SS-bond) of GSSG to help the progression of the derivative reaction. As an example, the blood sample and the reductant can be mixed, followed by microwaving at 750 Watts (W) for 1 minute. Thus, the reductant can break the disulfide bond of GSSG in the blood sample. The protein precipitant can then be added to remove the proteins in the blood sample. Finally, the supernatant, which can be used as the sample, is obtained. In this embodiment, dithiothreitol (DTT) can be used as the reductant. In addition, the reductant can be dissolved in water to form a reductant solution with a concentration of the reductant ranging from 0.025 mM to 25 mM.

Figure 3:
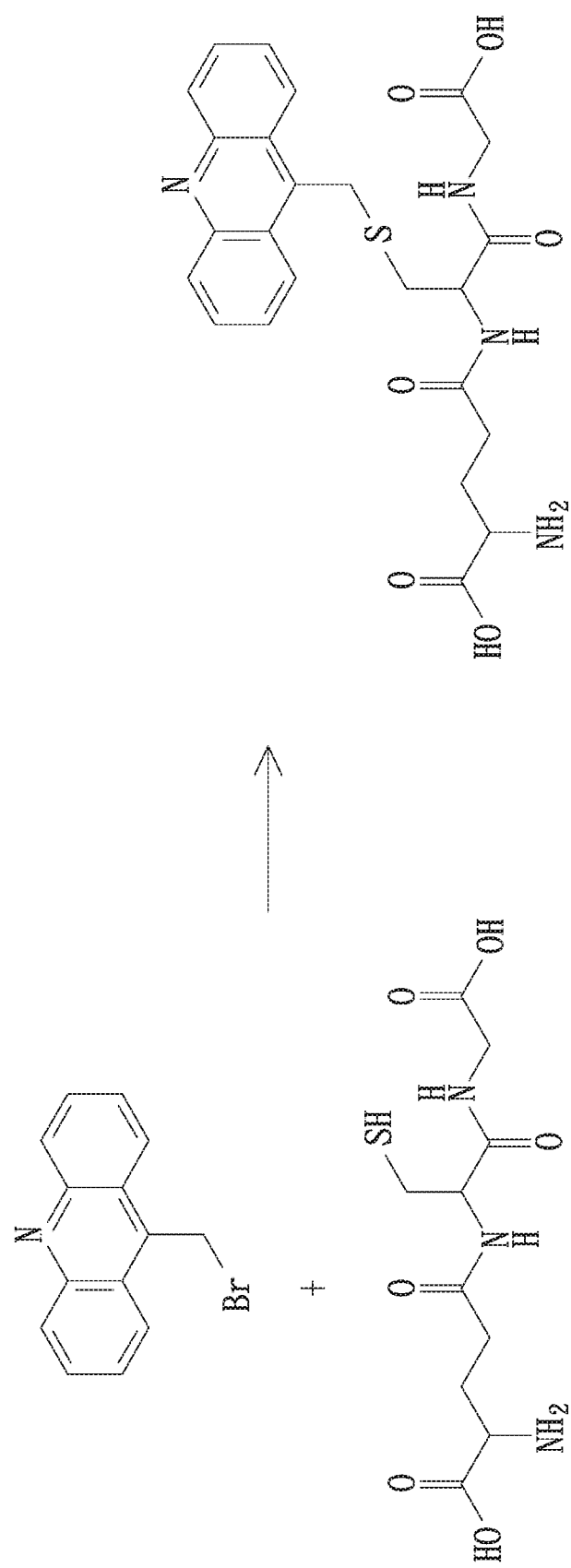
FIG. 3 depicts a chemical reaction of a derivative reaction between GSH and 9-bromomethyl acridine (Br-MA).
Figure 4:
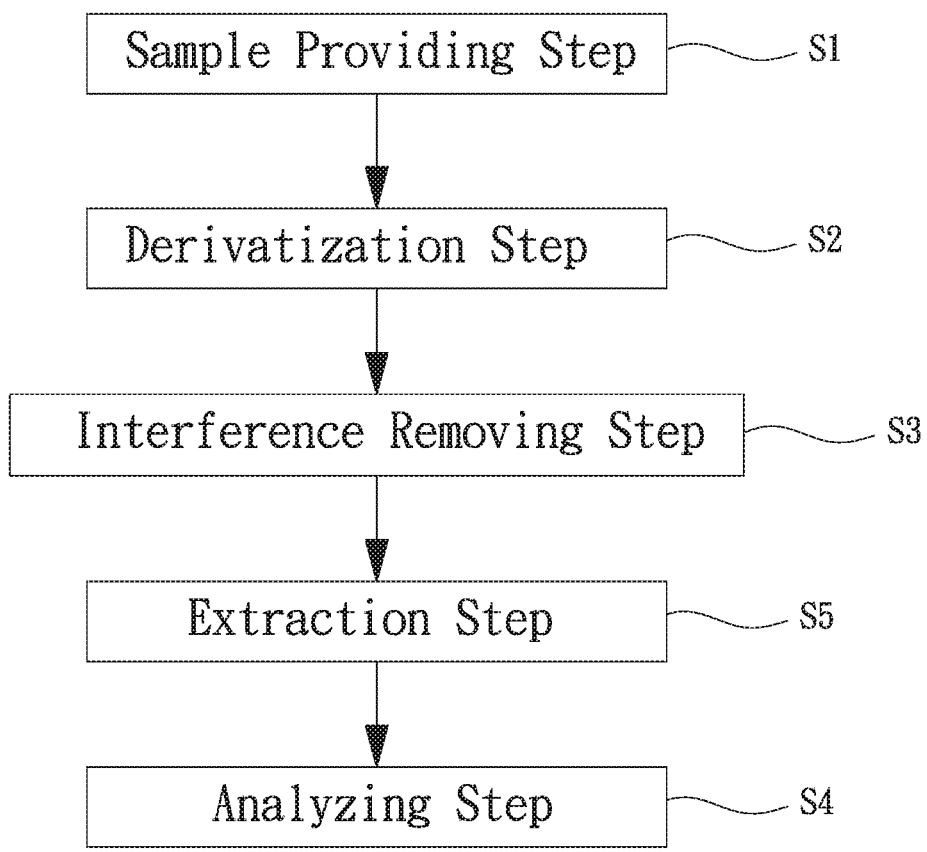
FIG. 4 depicts a flow chart illustrating a method for detecting glutathione according to a second embodiment of the present invention.

In the derivatization step S2, 9-bromomethyl acridine (Br-MA) can be used as the derivatization reagent, which is dissolved in a derivatization solvent. Br-MA dissolving in the derivatization solvent is added to the sample to form a reaction solution. Thus, the glutathione derivative can be formed via a derivative reaction, shown in FIG. 3, between glutathione in the sample and Br-MA, obtaining a derivatization solution. More detailedly, a thiol group (—SH) of glutathione deprotonates, attacking Br-MA and releasing a leaving group, that is, a bromide group (—Br⁻) from Br-MA. Thus, the formed glutathione derivative is a tagged glutathione, in which the thiol group of glutathione is substituted with a tag. In this embodiment, acetone, ACN or dimethyl sulfoxide (DMSO) can be used as the derivatization solvent. In addition, Br-MA can be dissolved in the derivatization solvent to form a Br-MA solution with a concentration of Br-MA ranging from 0.25 mM to 5 mM. It is worthy to note that considering solvent compatibility of the protein precipitant and the derivatization solvent, both the protein precipitant and the derivatization solvent can preferably be selected as acetone.

Preferably, glutathione and Br-MA can form the glutathione derivative in a basic environment. Therefore, a base catalyst can also be added in the reaction solution including the sample, Br-MA and the derivatization solvent. The base catalyst accelerates the deprotonation of the thiol group of glutathione and helps the progression of the derivative reaction. The base catalyst can be a base which is able to dissolve in the derivatization solvent. In this embodiment, sodium hydroxide (NaOH), potassium hydroxide (KOH), sodium bicarbonate ($NaHCO_3$) or potassium bicarbonate ($KHCO_3$) can be used as the base catalyst. Moreover, the base catalyst can be dissolved in water to form a base catalyst solution with a concentration of the base catalyst ranging from 0.5M to 1 M.

To accelerate the progression of the derivative reaction, energy can be applied to the reaction solution. As an example, energy can be applied to the reaction solution by microwaving the reaction solution. With such performance, molecular dipoles and/or ions in the reaction solution rotate and collide with other molecular dipoles and/or ions, producing thermal energy which increases collision frequency between glutathione and Br-MA in the reaction solution. Therefore, the glutathione derivative can be formed in a short time. In this embodiment, the reaction solution can be microwaved at 100-750 watts for 0.5-9 minutes.

In the interference removing step S3, an interference removing solvent is added in the derivatization solution. The interference removing solvent is immiscible with the reaction solution as well as the derivatization solution, and thus can be separated into layers after vortexing and centrifugation. A layer containing the glutathione derivative can be collected and excess Br-MA, hydrolysates of Br-MA and other interferences in the derivatization solution can be removed. In this embodiment, a Log P value of the interference removing solvent ranges from about 0.5 to about 2.0. As an example, ethyl acetate (EA), propyl acetate (PA) or tert-butyl acetate (BA) can be used as the interference removing solvent. Moreover, the interference removing solvent is added into the derivatization solution, followed by vortexing and centrifugation at 14,800 rpm for 1 minute to obtain an organic layer solution and an aqueous layer solution. The aqueous layer solution is then used as an analytic solution in the following analyzing step S4.

In the following analyzing step S4, glutathione derivative in the analytic solution can be detected by any conventional analytical techniques to obtain the glutathione value. The glutathione value can be used to estimate whether glutathione is present in the sample, or even to estimate glutathione level in the sample. Specifically, the glutathione derivative in the analytic solution can be detected by liquid chromatography or mass spectrometry. As an example, the glutathione derivative in the analytic solution can be detected by liquid chromatography capillary high performance liquid chromatography (CapLC) or by nano-liquid chromatography (nano-LC) coupled to mass spectrometry. Moreover, the glutathione derivative formed by glutathione together with Br-MA can also be detected by ultra violet (UV) spectroscopy or fluorescence spectroscopy, obtaining the glutathione value.

Besides, the method for detecting glutathione according to a second embodiment of the present invention is approximately the same as the method according to the first embodiment of the present invention. The main difference between the method according to the second and the first embodiments is an extraction step S5 is performed between the interference removing step S3 and the analyzing step S4.

Specifically, in the extraction step S5, a cationic surfactant used as an extractant is added in the aqueous layer solution. The glutathione derivative, formed by glutathione with a carboxyl group (—COOH), dissociates and forms a carboxylate anion (—COO⁻). Therefore, the cationic surfactant with positive charge attracts the glutathione derivative with negatively charged carboxylate anion to extract the glutathione derivative in the aqueous layer solution, obtaining an extract. Moreover, the cationic surfactant has a carbon number between 25 and 32, and thus, not only an electrostatic attraction but also a hydrophobic interaction is formed between the cationic surfactant and the glutathione derivative, increasing extraction efficiency. In this embodiment, trioctylmethylammonium chloride (A336), tetraheptylammonium bromide (THepAB) or tetraoctylammonium bromide (TOAB) can be used as the cationic surfactant. In addition, the cationic surfactant can be dissolved in methanol to form a cationic surfactant solution with a concentration of the cationic surfactant ranging from 1.5 M to 3.5 M.

Accordingly, based on the same technical concept, a kit for detecting glutathione according to an embodiment of the present invention can include the derivatization reagent, the derivatization solvent and the interference removing solvent. The derivatization reagent, Br-MA, is used to form the glutathione derivative together with glutathione via the derivative reaction. The derivatization solvent, such as acetone, ACN or DMSO, is a solvent able to dissolve Br-MA and glutathione. The interference removing solvent, a solvent immiscible with the reaction solution as well as the derivatization solution, is used to remove the excess Br-MA and the hydrolysates of Br-MA (MA-OH) in the derivatization solution. The interference removing solvent, such as EA, PA or BA, preferably has the Log P value ranging from about 0.5 to about 2.0.

Moreover, the kit for detecting glutathione can also include the base catalyst. The base catalyst, such as NaOH, KOH, $NaHCO_3$ or $KHCO_3$, is the base able to dissolve in the derivatization solvent and is used to provide the basic environment for the derivative reaction.

In addition, the kit for detecting glutathione can further include the cationic surfactant. The cationic surfactant, such as A336, THepAB or TOAB, has the carbon number between 25 and 32, and is used to extract the glutathione derivative.

To evaluate the method for detecting glutathione according to the second embodiment of the present invention can be used to detect glutathione level in the RBC sample, 40 μM of glutathione is used as a standard. The RBC sample (15 μL), glutathione (120 μL) and acetone (165 μL, used as the protein precipitant) are mixed, followed by vortexing and centrifugation to obtain the supernatant, which is used as the sample. The sample (280 μL), Br-MA (35 μL, used as the derivatization reagent and dissolved in acetone as the derivatization solvent with the concentration of Br-MA being 0.5 mM) and NaOH (5 μL, used as the base catalyst and dissolved in water with the concentration of NaOH being 0.5 M) are mixed to obtain the reaction solution. The reaction solution is microwaved at 550 watts for 1 minute to obtain the derivatization solution. BA (350 μL, used as the interference removing solvent) is added into the derivatization solution, followed by vortexing and centrifugation to obtain the aqueous layer solution. A336 (25 μL, used as the cationic surfactant and dissolved in methanol with the concentration of A336 being 1.5 M) is added into the aqueous layer solution, followed by vortexing and centrifugation to obtain the extract (8 μL). The extract is diluted with methanol until a total volume of a mixture containing the extract and methanol is 25 μL. Finally, the extract (0.5 μL) is used as the analytic solution, and the glutathione value is detected by CapLC.

Trial (A).

The sample, the derivatization reagent listed in TABLE 1 and NaOH (the base catalyst) are mixed to obtain the reaction solution. The reaction solution is microwaved to obtain the derivatization solution. BA (the interference removing solvent) is added into the derivatization solution, followed by vortexing and centrifugation to obtain the aqueous layer solution. A336 (the cationic surfactant) is added into the aqueous layer solution, followed by vortexing and centrifugation to obtain the extract. The extract is then used as the analytic solution, and the glutathione value is detected by CapLC.

TABLE 1

| Group | Derivatization reagent |
|---|---|
| A1 | 9-bromomethyl acridine (Br-MA) |
| A2 | 4-bromomethyl biphenyl (Br-MMP) |
| A3 | 7-acetoxy-4-bromomethyl coumarin (Br-MAC) |
| A4 | 2-bromomethyl naphthalene (Br-MN) |
| A5 | 3-bromomethyl-7-methoxy-1,4-benzoxazin-2-one (Br-MMB) |
| A6 | 1-bromoacetyl pyrene (Br-AP) |
| A7 | 3-bromoacetyl coumarin (Br-AC) |
| A8 | 2-(bromomethyl)-6-methylpyridine (Br-MP) |

Figure 5:
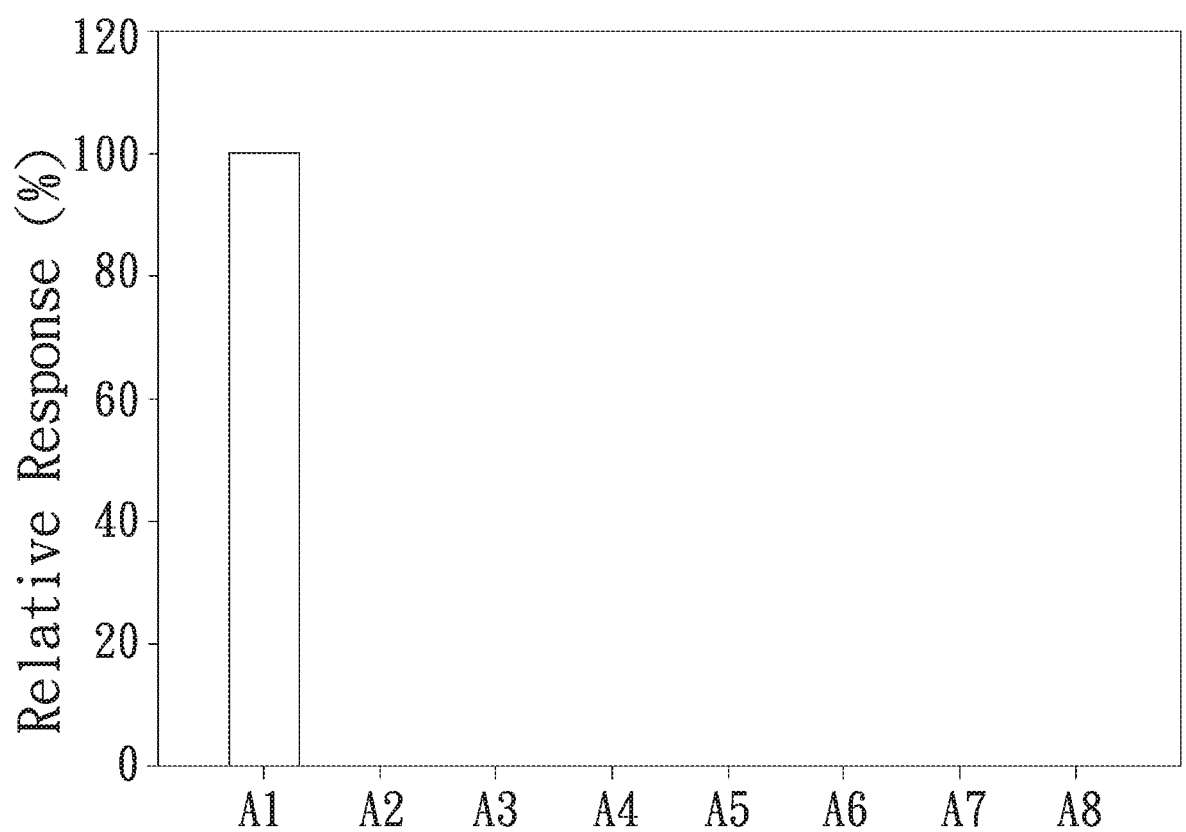
FIG. 5 depicts a bar chart illustrating relative response (glutathione value) of groups A1 to A8 obtained by the method for detecting glutathione according to the second embodiment of the present invention in trial (A).

Referring to FIG. 5, group A1 with the derivatization reagent being Br-MA has the highest glutathione value compared to groups A2 to A8, indicating the use of Br-MA as the derivatization reagent shows a preferable efficiency in the method for detecting glutathione according to the second embodiment.

Trial (B).

The sample, Br-MA (the derivatization reagent) and the base catalyst listed in TABLE 2 are mixed to obtain the reaction solution. The reaction solution is microwaved to obtain the derivatization solution. BA (the interference removing solvent) is added into the derivatization solution, followed by vortexing and centrifugation to obtain the aqueous layer solution. A336 (the cationic surfactant) is added into the aqueous layer solution, followed by vortexing and centrifugation to obtain the extract. The extract is then used as the analytic solution, and the glutathione value is detected by CapLC.

TABLE 2

| Group | Base catalyst (dissolved in water) |
|---|---|
| B1 | sodium hydroxide (NaOH) |
| B2 | potassium hydroxide (KOH) |

TABLE 2-continued

| Group | Base catalyst (dissolved in water) |
|---|---|
| B3 | sodium bicarbonate (NaHCO$_3$) |
| B4 | potassium bicarbonate (KHCO$_3$) |

Figure 6A:
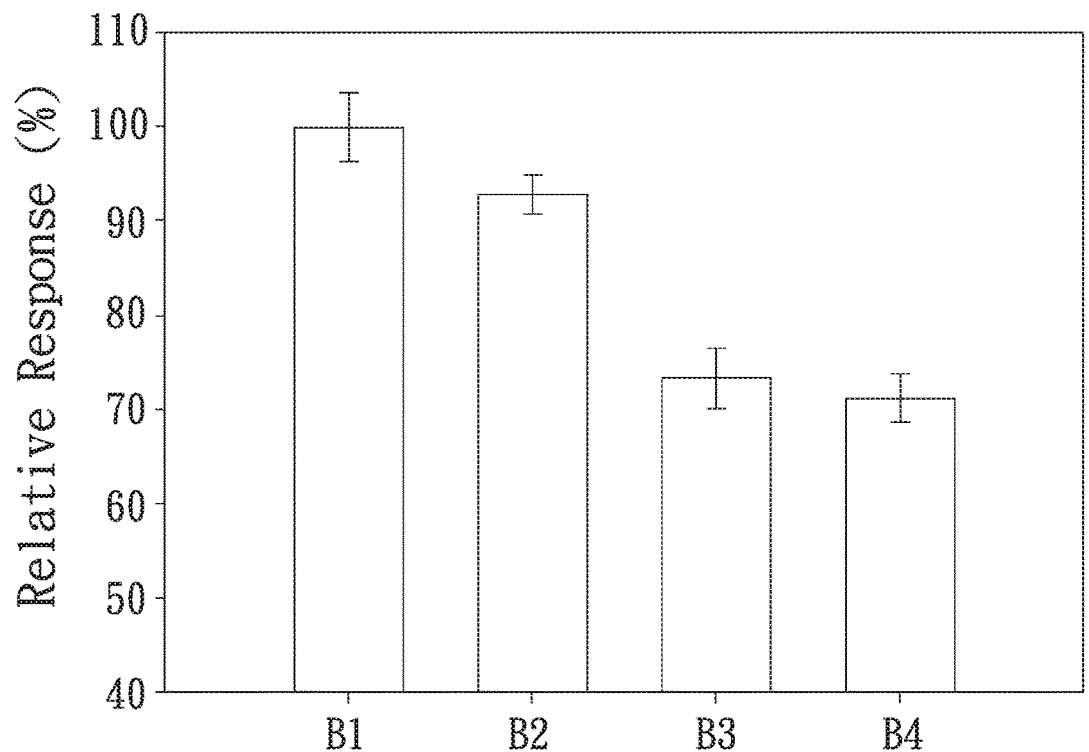
FIG. 6a depicts a bar chart illustrating relative response (glutathione value) of groups B1 to B4 obtained by the method for detecting glutathione according to the second embodiment of the present invention in trial (B).

Referring to FIG. 6a, groups B1 and B2 with the base catalyst being NaOH and KOH, respectively, have higher glutathione value compared to groups B3 and B4, indicating the use of NaOH, as well as KOH, as the base catalyst shows a preferable efficiency in the method for detecting glutathione according to the second embodiment. Additionally, group B1 shows a better efficiency compared to group B2.

Moreover, the sample, Br-MA (the derivatization reagent) and NaOH (the base catalyst) with different concentration listed in TABLE 3 are mixed to obtain the reaction solution. The reaction solution is microwaved to obtain the derivatization solution. BA (the interference removing solvent) is added into the derivatization solution, followed by vortexing and centrifugation to obtain the aqueous layer solution. A336 (the cationic surfactant) is added into the aqueous layer solution, followed by vortexing and centrifugation to obtain the extract. The extract is then used as the analytic solution, and the glutathione value is detected by CapLC.

TABLE 3

| Group | NaOH concentration (dissolved in water) |
|---|---|
| B1-1 | 0.05 M |
| B1-2 | 0.1 M |
| B1-3 | 0.5 M |
| B1-4 | 1 M |
| B1-5 | 2.5 M |
| B1-6 | 5 M |

Figure 6B:
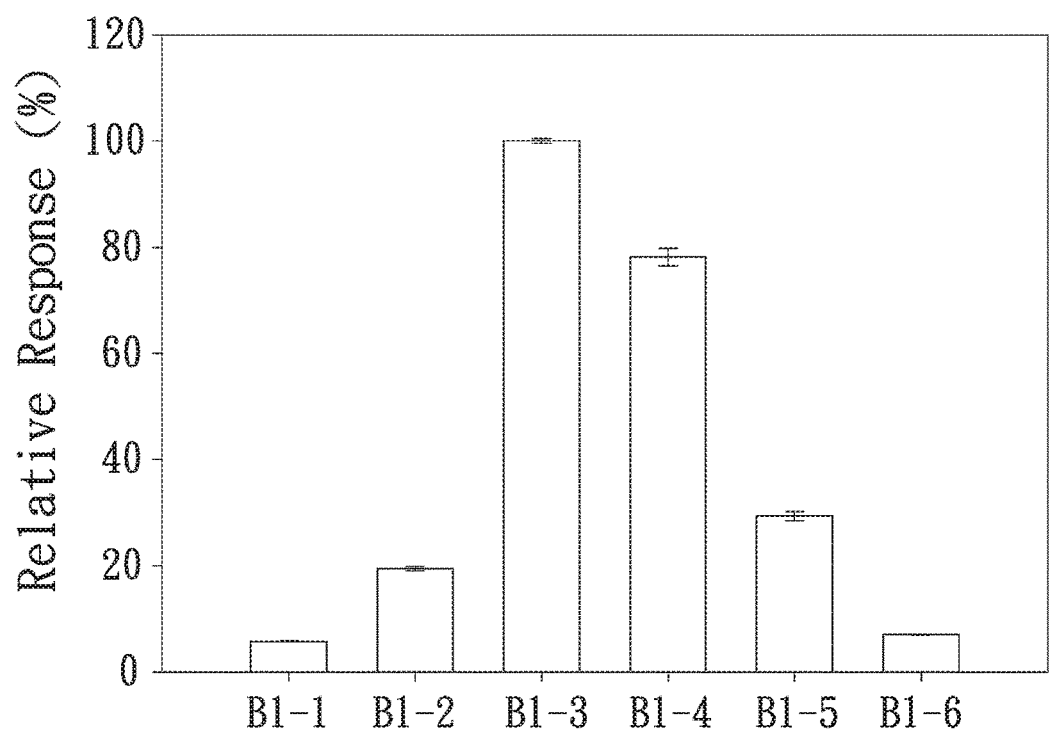
FIG. 6b depicts a bar chart illustrating relative response (glutathione value) of groups B1-1 to B1-6 obtained by the method for detecting glutathione according to the second embodiment of the present invention in trial (B).

Referring to FIG. 6b, group B1-3 with concentration of 0.5 M (group B1-3) has the highest glutathione value compared to groups B1-1, B1-2, B1-4, B1-5 and B1-6.

Trial (C).

The sample, Br-MA (the derivatization reagent) and NaOH (the base catalyst) are mixed to obtain the reaction solution. The reaction solution is microwaved to obtain the derivatization solution. The interference removing solvent listed in TABLE 4 is added into the derivatization solution, followed by vortexing and centrifugation to obtain the aqueous layer solution. A336 (the cationic surfactant) is added into the aqueous layer solution, followed by vortexing and centrifugation to obtain the extract. The extract is then used as the analytic solution, and the glutathione value is detected by CapLC.

TABLE 4

| Group | Interference removing solvent |
|---|---|
| C1 | ethyl acetate (EA) |
| C2 | propyl acetate (PA) |
| C3 | tert-butyl acetate (BA) |

Figure 7:
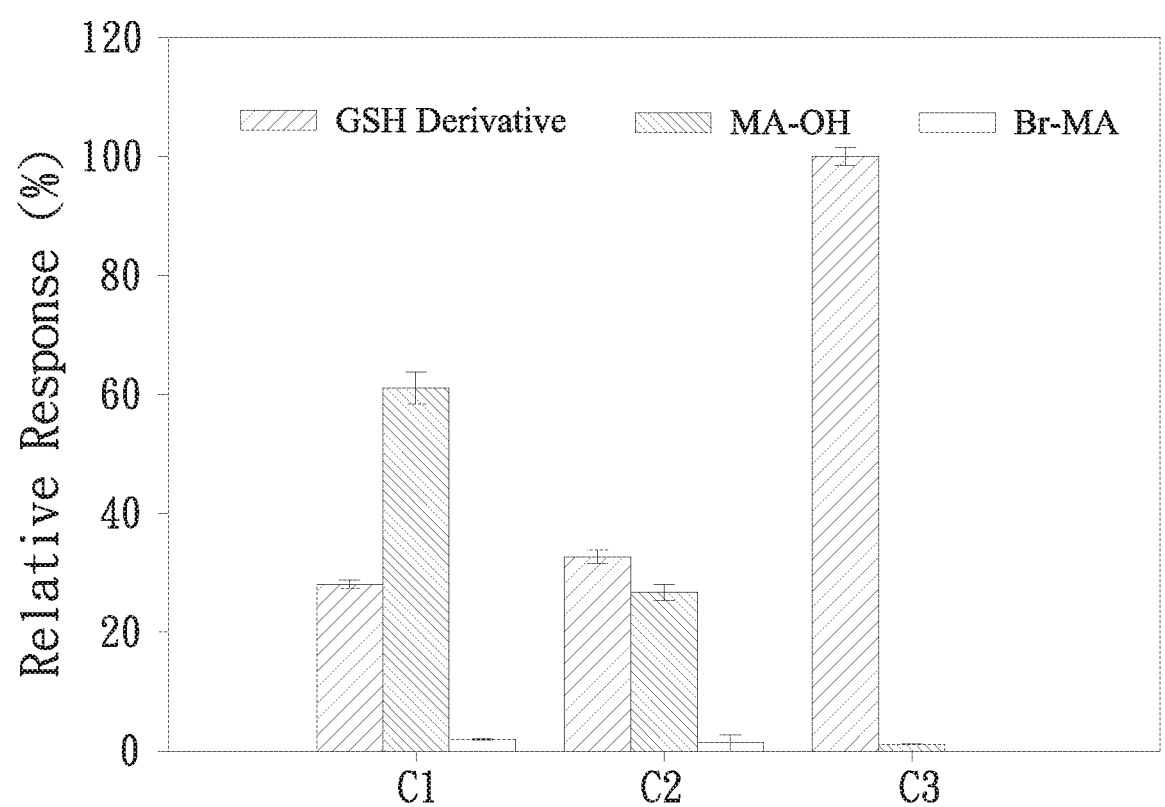
FIG. 7 depicts a bar chart illustrating relative response (glutathione value) of groups C1 to C3 obtained by the method for detecting glutathione according to the second embodiment of the present invention in trial (C).

Referring to FIG. 7, the interference removing solvent of group C3 shows the highest efficiency of removing excess Br-MA and the hydrolysates of Br-MA (MA-OH), and has the highest glutathione value (GSH derivative), compared to groups C1 and C2, indicating the use of BA as the interference removing solvent shows a preferable efficiency in the method for detecting glutathione according to the second embodiment.

Trial (D).

The sample, Br-MA (the derivatization reagent) and NaOH (the base catalyst) are mixed to obtain the reaction solution. The reaction solution is microwaved to obtain the derivatization solution. BA (the interference removing solvent) is added into the derivatization solution, followed by vortexing and centrifugation to obtain the aqueous layer solution. The cationic surfactant listed in TABLE 5 is added into the aqueous layer solution, followed by vortexing and centrifugation to obtain the extract. The extract is then used as the analytic solution, and the glutathione value is detected by CapLC.

TABLE 5

| Group | Cationic surfactant |
|---|---|
| D1 | tetra-N-hexylammonium bromide (THAB) |
| D2 | trioctylmethylammonium chloride (A336) |
| D3 | tetraheptylammonium bromide (THepAB) |
| D4 | tetraoctylammonium bromide (TOAB) |

Figure 8:
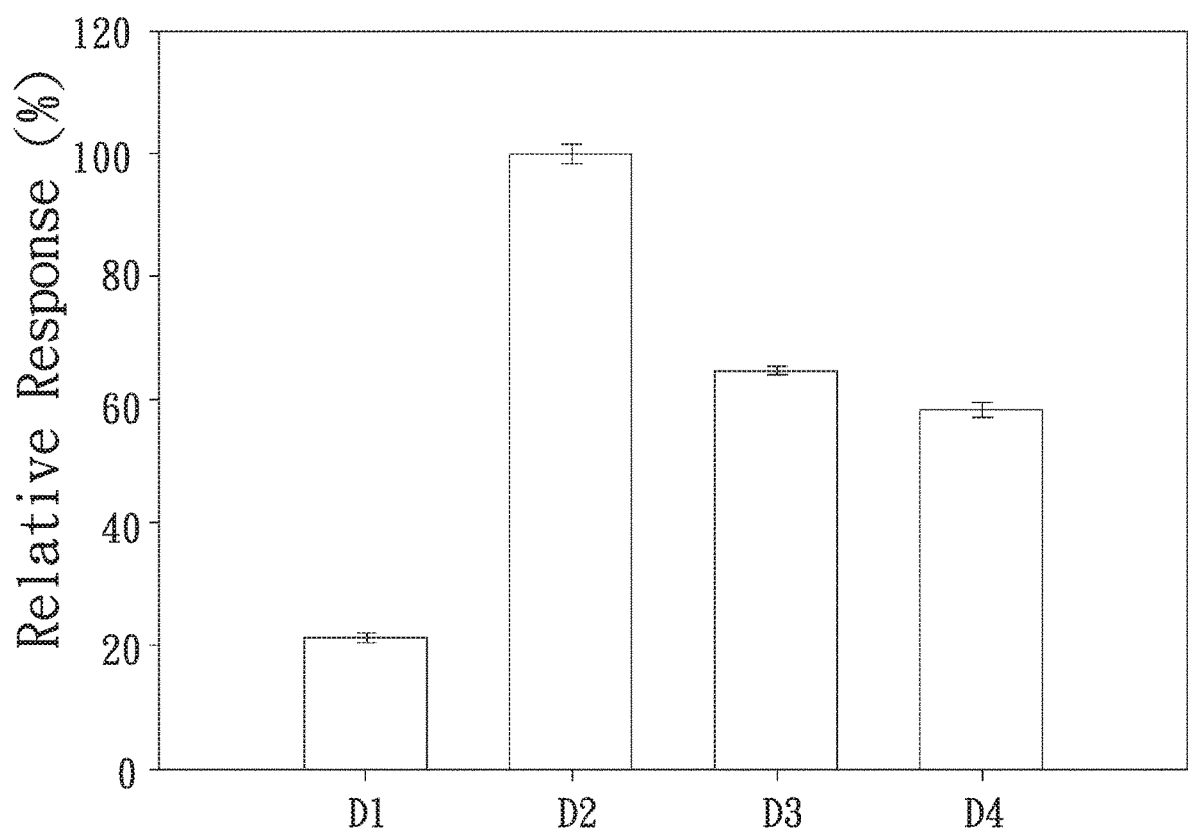
FIG. 8 depicts a bar chart illustrating relative response (glutathione value) of groups D1 to D4 obtained by the method for detecting glutathione according to the second embodiment of the present invention in trial (D).

Referring to FIG. 8, group D2 with the cationic surfactant being A336 has the highest glutathione value compared to groups D1, D3, and D4, indicating the use of A336 as the cationic surfactant shows a preferable efficiency in the method for detecting glutathione according to the second embodiment.

Trial (E).

Referring to TABLE 6, the derivatization solution without removing the interferences by BA (the interference removing solvent) as well as extracting by A336 (the cationic surfactant) is used as the analytic solution of group E1. The aqueous layer solution without extracting by A336 (the cationic surfactant) is used as the analytic solution of group E2, which is the analytic solution used in the first embodiment of the present invention). The extract is used as the analytic solution of group E3, which is the analytic solution used in the second embodiment of the present invention). The analytic solutions of groups E1 to E3 are analyzed by CapLC, respectively.

TABLE 6

| Group | Sample providing step, S1 | Derivatization step, S2 | Interference removing step, S3 | Extraction step S5 | Analyzing step, S4 |
|---|---|---|---|---|---|
| E1 | + | + | − | − | + |
| E2 | + | + | + | − | + |
| E3 | + | + | + | + | + |

Figure 9:
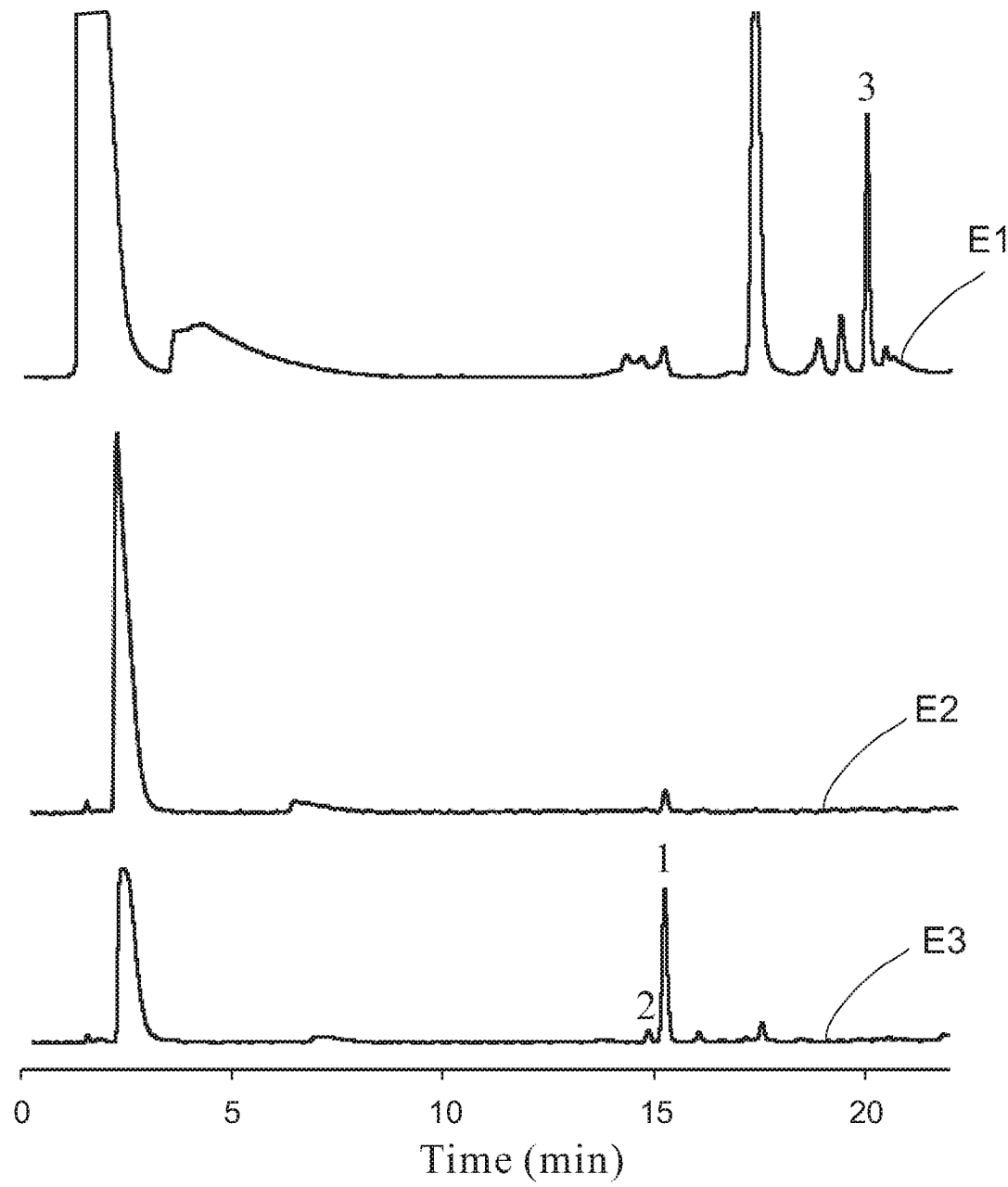
FIG. 9 depicts chromatograms illustrating relative response of groups E1 to E3 obtained by the method for detecting glutathione according to the first and second embodiments of the present invention in trial (E). Peak 1 shows glutathione, peak 2 shows hydrolysates of Br-MA (MA-OH) and peak 3 shows Br-MA.

Referring to FIG. 9, compared to the analytic solution of group E1, the analytic solution of group E2 has fewer peaks, indicating the performance of the interference removing step S3 help removing the inferences, such as excess Br-MA, in the derivatization solution. Moreover, the analytic solution of group E3 has a higher peak representing the glutathione derivative, indicating the interference removing step S3 and the extraction step S5 show synergetic effect on the method for detecting glutathione according to the second embodiment.

Furthermore, to evaluate the method for detecting glutathione according to the second embodiment of the present invention can be used to detect GSSG (oxidized glutathione) level in the RBC sample, following trials are carried out. The RBC sample (15 μL), glutathione (40 μM, 120 μL) and DTT (20 μL, used as the reductant) are mixed, followed by breaking the disulfide bond of GSSG by microwaving (750 W, 1 minute). Acetone (165 μL, used as the protein precipitant) is then added, followed by vortexing and centrifugation to obtain the supernatant, which is used as the sample. The sample (280 μL), Br-MA (35 μL, used as the derivatization reagent and dissolved in acetone as the derivatization solvent with the concentration of Br-MA being 0.5 mM) and NaOH (5 μL, used as the base catalyst and dissolved in water with the concentration of NaOH being 0.5 M) are mixed to obtain the reaction solution. The reaction solution is microwaved at 550 watts for 1 minute to obtain the derivatization solution. BA (350 μL, used as the interference removing solvent) is added into the derivatization solution, followed by vortexing and centrifugation to obtain the aqueous layer solution. A336 (25 μL, used as the cationic surfactant and dissolved in methanol with the concentration of A336 being 1.5 M) is added into the aqueous layer solution, followed by vortexing and centrifugation to obtain the extract (8 μL). The extract is diluted with methanol until a total volume of a mixture containing the extract and methanol is 25 μL. Finally, the extract (0.5 μL) is used as the analytic solution, and the glutathione value is detected by CapLC.

Trial (F).

The RBC sample, glutathione and the reductant listed in TABLE 7 are mixed, followed by breaking the disulfide bond of GSSG Acetone (the protein precipitant) is then added, followed by vortexing and centrifugation to obtain the supernatant, which is used as the sample. The sample, Br-MA (the derivatization reagent) and NaOH (the base catalyst) are mixed to obtain the reaction solution. The reaction solution is microwaved to obtain the derivatization solution. BA (the interference removing solvent) is added into the derivatization solution, followed by vortexing and centrifugation to obtain the aqueous layer solution. A336 (the cationic surfactant) is added into the aqueous layer solution, followed by vortexing and centrifugation to obtain the extract. The extract is then used as the analytic solution, and the glutathione value is detected by CapLC.

TABLE 7

| Group | Reductant |
|---|---|
| F1 | dithiothreitol (DTT) |
| F2 | tris(2-carboxyethyl)phosphine hydrochloride (TCEP) |

Figure 10:
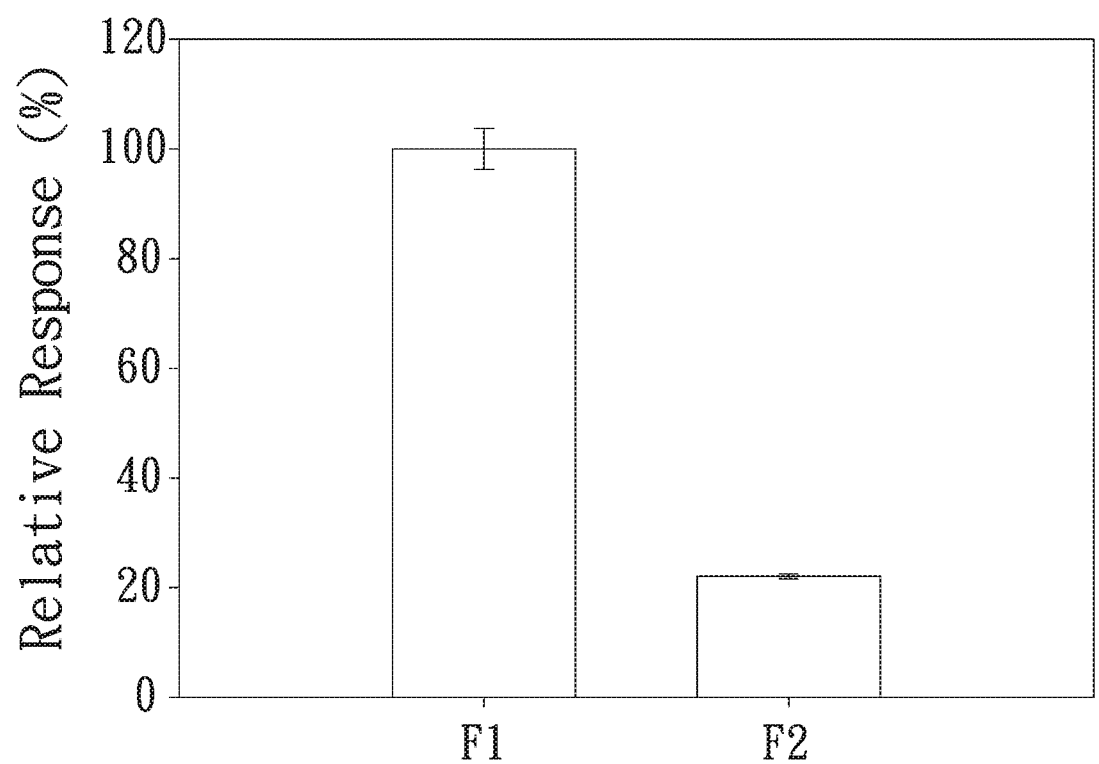
FIG. 10 depicts a bar chart illustrating relative response (glutathione value) of groups F1 to F3 obtained by the method for detecting glutathione according to the second embodiment of the present invention in trial (F).

Referring to FIG. 10, group F1 with the reductant being DTT has a higher glutathione value compared to group F2, indicating the use of DTT as the reductant show a preferable efficiency in the method for detecting glutathione according to the second embodiment.

Trial (G).

Glutathione (0, 0.12, 0.6, 2.4 and 4.8 nmol) is added into the RBC samples derived from 5 healthy adults. The glutathione value is obtained by the method for detecting glutathione according to the second embodiment of the present invention. Reduced glutathione (GSH) level in the RBC sample is calculated by the glutathione value obtained without DTT (the reductant). Total glutathione (tGSH) level in the RBS sample is calculated by the glutathione value obtained with DTT. The oxidized glutathione (GSSG) level is calculated by subtracting the GSH level from the tGSH level.

TABLE 8

| Sample No. | GSH level (μM) | tGSH level (μM) | GSSG level (μM) | GSH/GSSG |
|---|---|---|---|---|
| #01 | 1486.7 ± 17.1 | 1649.2 ± 23.3 | 162.4 ± 6.3 | 9.15 |
| #02 | 1028.7 ± 12.3 | 1114.3 ± 12.8 | 85.7 ± 1.3 | 12.01 |
| #03 | 838.4 ± 41.8 | 914.5 ± 43.1 | 76.1 ± 1.8 | 11.01 |
| #04 | 664.0 ± 23.5 | 729.0 ± 24.7 | 65.0 ± 1.3 | 10.21 |
| #05 | 649.7 ± 9.2 | 712.1 ± 8.3 | 62.4 ± 2.1 | 10.42 |

Referring to TABLE 8, calculated ratio of the GSH level to the GSSG level (GSH/GSSG) ranges from 9.15 to 12.01, conforming to the GSH/GSSG ratio of healthy adults.

Accordingly, by the use of Br-MA, the glutathione derivative with great stability is formed together with glutathione, and can be detected by any conventional analytical techniques, such as ultra violet spectroscopy, fluorescence spectroscopy, liquid chromatography or mass spectrometry. Therefore, the method for detecting glutathione according to the present invention has great sensitivity, decreasing sample amount.

Moreover, the kit for detecting glutathione according to the present invention can be adapted to carry out the method for detecting glutathione. The glutathione derivative with great stability can be formed together with glutathione, and can be detected by any conventional analytical techniques, such as ultra violet spectroscopy, fluorescence spectroscopy, liquid chromatography or mass spectrometry, according to demands.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A method for detecting glutathione, comprising:
   mixing a sample including glutathione, 9-bromomethyl acridine and a derivatization solvent to form a reaction solution;
   triggering a derivative reaction between 9-bromomethyl acridine and glutathione to obtain a derivatization solution including a glutathione derivative with a thiol group being substituted with a tag, wherein the tag is a portion of 9-bromomethyl acridine that is reacted with glutathione;
   removing excessive 9-bromomethyl acridine by adding an interference removing solvent into the derivatization solution, followed by vortexing and centrifugation to obtain an aqueous layer solution including the glutathione derivative; and
   detecting the glutathione derivative in an analytic solution to obtain a glutathione value, wherein the aqueous layer solution is used as the analytic solution.

2. The method for detecting glutathione as claimed in claim 1, wherein the derivatization solvent is selected from acetone, acetonitrile or dimethyl sulfoxide.

3. The method for detecting glutathione as claimed in claim 1, wherein the method further comprises: adding a base catalyst into the reaction solution, followed by triggering the derivative reaction occurs in the reaction solution dissolving the base catalyst to obtain the derivatization solution.

4. The method for detecting glutathione as claimed in claim 3, wherein the derivatization solvent is selected from acetone, acetonitrile or dimethyl sulfoxide, and the base catalyst is selected from sodium hydroxide, potassium hydroxide, sodium bicarbonate or potassium bicarbonate.

5. The method for detecting glutathione as claimed in claim 4, wherein the interference removing solvent is selected from ethyl acetate, propyl acetate or tert-butyl acetate.

6. The method for detecting glutathione as claimed in claim 1, wherein the method further comprises: extracting the glutathione derivative in the aqueous layer solution by a cationic surfactant to obtain an extract, which is used as the analytic solution.

7. The method for detecting glutathione as claimed in claim 6, wherein the interference removing solvent is selected from ethyl acetate, propyl acetate or tert-butyl acetate; and the cationic surfactant is selected from trioctylmethylammonium chloride, tetrahepatylammonium bromide or tetraoctylammonium bromide.

8. The method for detecting glutathione as claimed in claim 1, wherein the method further comprises:
   mixing a blood sample and a protein precipitant, assuring proteins in the blood sample form a protein precipitate; and
   removing the protein precipitate by centrifugation to obtain a supernatant, which is used as the sample.

9. The method for detecting glutathione as claimed in claim 8, wherein the protein precipitant is selected from acetone or acetonitrile.

10. The method for detecting glutathione as claimed in claim 1, wherein the method further comprises:
    mixing a blood sample and a reductant to break a disulfide bond of glutathione in the blood sample; and
    obtaining a supernatant, which is used as the sample, by centrifugation to remove a protein precipitate forming by adding a protein precipitant into the blood sample, in which the disulfide bond of glutathione is broken.

11. The method for detecting glutathione as claimed in claim 10, wherein the reductant is dithiothreitol, and the protein precipitant is selected from acetone or acetonitrile.

12. The method for detecting glutathione as claimed in claim 1, wherein the glutathione derivative in the analytic solution is detected by ultra violet spectroscopy, fluorescence spectroscopy, liquid chromatography or mass spectrometry to obtain the glutathione value.

13. A kit for detecting glutathione, used to detect whether glutathione is present in a sample, comprising:
    9-bromomethyl acridine used to form a glutathione derivative together with glutathione in the sample, wherein the glutathione derivative has a thiol group substituted with a tag, wherein the tag is a portion of 9-bromomethyl acridine that is reacted with glutathione;
    a derivatization solvent being a solvent able to dissolve 9-bromomethyl acridine and glutathione, wherein the derivatization solvent is used to form a reaction solution together with the sample and 9-bromomethyl acridine, wherein the derivatization solvent is selected from acetone, acetonitrile or dimethyl sulfoxide;
    an interference removing solvent being a solvent immiscible with the reaction solution, wherein a Log P value of the interference removing solvent ranges from 0.5 to 2.0, wherein the interference removing solvent is used to remove excessive 9-bromomethyl acridine in a derivatization solution, wherein the derivatization solution is formed via a derivative reaction between 9-bromomethyl acridine and glutathione in the sample; and a base catalyst being a base able to dissolve in the derivatization solvent, wherein the base catalyst is used to provide a basic environment for the derivative reaction.

14. The kit for detecting glutathione as claimed in claim 13, wherein the base catalyst is selected from sodium hydroxide, potassium hydroxide, sodium bicarbonate or potassium bicarbonate.

15. The kit for detecting glutathione as claimed in claim 13, wherein the interference removing solvent is selected from ethyl acetate, propyl acetate or tert-butyl acetate.

16. A kit for detecting glutathione, used to detect whether glutathione is present in a sample, comprising:
   9-bromomethyl acridine used to form a glutathione derivative together with glutathione in the sample, wherein the glutathione derivative has a thiol group substituted with a tag, wherein the tag is a portion of 9-bromomethyl acridine that is reacted with glutathione;
   a derivatization solvent being a solvent able to dissolve 9-bromomethyl acridine and glutathione, wherein the derivatization solvent is used to form a reaction solution together with the sample and 9-bromomethyl acridine;
   an interference removing solvent being a solvent immiscible with the reaction solution, wherein a Log P value of the interference removing solvent ranges from 0.5 to 2.0, wherein the interference removing solvent is used to remove excessive 9-bromomethyl acridine in a derivatization solution, wherein the derivatization solution is formed via a derivative reaction between 9-bromomethyl acridine and glutathione in the sample; and
   a cationic surfactant with a carbon number ranging from 25 to 32, wherein the cationic surfactant is used to extract the glutathione derivative from an aqueous layer solution, wherein the aqueous layer solution is formed by vortexing and centrifugation the derivatization solution including the interference removing solvent.

17. The kit for detecting glutathione as claimed in claim 16, wherein the cationic surfactant is selected from trioctylmethylammonium chloride, tetraheptylammonium bromide or tetraoctylammonium bromide.

18. The kit for detecting glutathione as claimed in claim 16, wherein the derivatization solvent is selected from acetone, acetonitrile or dimethyl sulfoxide.

19. The kit for detecting glutathione as claimed in claim 18, wherein the kit further comprises: a base catalyst being a base able to dissolve in the derivatization solvent, wherein the base catalyst is used to provide a basic environment for the derivative reaction.

20. The kit for detecting glutathione as claimed in claim 19, wherein the base catalyst is selected from sodium hydroxide, potassium hydroxide, sodium bicarbonate or potassium bicarbonate.

21. The kit for detecting glutathione as claimed in claim 16, wherein the interference removing solvent is selected from ethyl acetate, propyl acetate or tert-butyl acetate.

* * * * *